US006309398B1

United States Patent
Flörke

(12) United States Patent
(10) Patent No.: US 6,309,398 B1
(45) Date of Patent: Oct. 30, 2001

(54) HORNY SKIN REMOVER

(76) Inventor: Armin Flörke, Bürgermeister-Mahr-Strasse 28, 63179 Obertshausen (DE)

( * ) Notice: Subject to any disclaimer, the term of this patent is extended or adjusted under 35 U.S.C. 154(b) by 0 days.

(21) Appl. No.: 09/704,280

(22) Filed: Nov. 1, 2000

(30) Foreign Application Priority Data

Nov. 3, 1999 (DE) .............................. 299 19 293

(51) Int. Cl.[7] .................................................. A61B 17/50
(52) U.S. Cl. .............................. 606/131; 30/30; 132/73.5
(58) Field of Search ................................... 606/131, 132, 606/133, 159; 600/562, 569; 604/289, 290, 313, 315; 132/73, 75.6, 75.8, 73.5; 30/30, 32

(56) References Cited

U.S. PATENT DOCUMENTS 4,122,855 * 10/1978 Tezel .................................... 606/131
4,441,252 * 4/1984 Caves .................................... 30/30
4,663,841 * 5/1987 Custer .................................. 30/30
5,620,455 * 4/1997 Grigoletto .......................... 606/131

FOREIGN PATENT DOCUMENTS

8631541 * 2/1987 (DE) .................................... 606/131

* cited by examiner

Primary Examiner—Pedro Philogene
(74) Attorney, Agent, or Firm—Cristina M Offenberg

(57) ABSTRACT

The present invention is concerned with a horny skin remover, comprising a handle and a header mounted thereon attached to which, by a clamp, is a blade having at least one cutting edge. The horny skin remover has a double function of the clamp, using it both for attaching and for covering the blade in times of non-use, thereby eliminating a separate blade protection otherwise required, and at the same time insuring that protection of the blade not be forgotten, by inadvertence, as the clamp is required for mounting the blade. The blade itself is protected, when the skin remover is not used. The clamp adjustable in relation to the blade is associated to the header and has at least two adjustable positions, namely the "RELEASE" and the "COVER" positions.

10 Claims, 3 Drawing Sheets

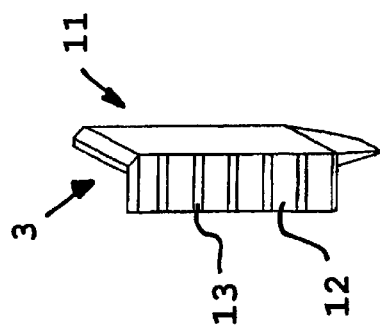
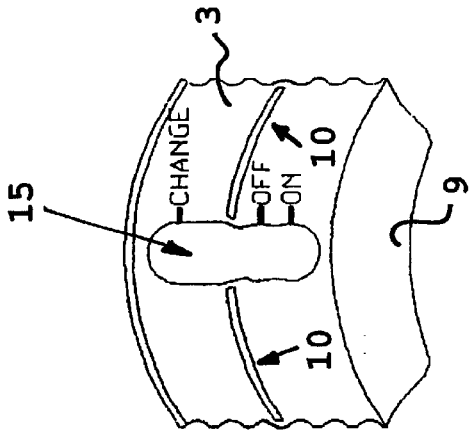
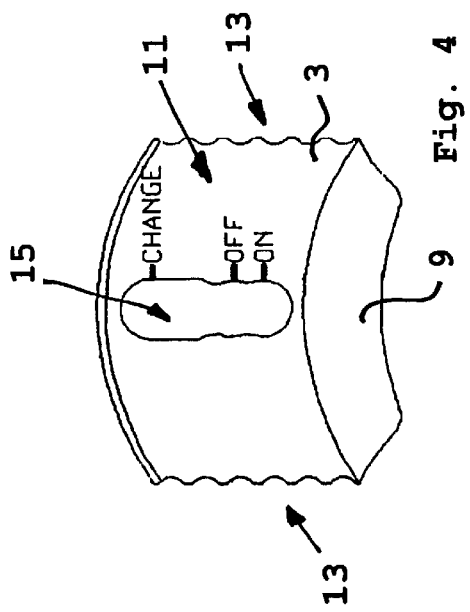
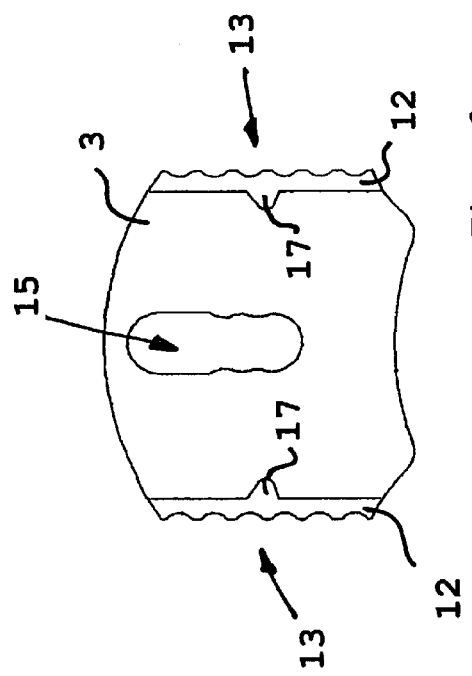

HORNY SKIN REMOVER

BACKGROUND OF THE INVENTION

1. Field of the Invention

The present invention is concerned with a horny skin remover, comprising a handle and a header mounted thereon attached to which, by means of a clamp, is a blade having at least one cutting edge.

2. Description of Prior Art

Horny skin removers of the afore-mentioned type are known in the art as disclosed, for example, by DE 86 31 541 U1. They serve to remove undesirable horny skin, in particular, on a person's heels. The blade with the cutting edge thereof is directed toward the handle to be guided, in a drawing movement, across the horny skin which is removed in thin layers. The blade, in the majority of cases, is replaceably attached to the skin remover. However, also so-called "disposable skin removers" are known in the art.

In the horny skin remover of the afore-mentioned type, replacement of the blade is effected by urging the clamp along with the blade into a position of replacement wherein both the clamp and the blade can be separated from the header. Clamp and blade, during displacement, maintain their relative position with respect to one another. Blades having two cutting edges can be readily turned round in the position of replacement.

Once the blade is mounted, it is clamped between header and clamping unit. Provided on the header, in the area of the cutting edge, is a gap for discharging the removed horny skin. The razor-type blade protrudes only a few millimeters beyond the clamp in order to be able to withstand the mechanical load.

Basically, horny skin removers of this type have proved highly satisfactory, especially so as far as the cutting performance thereof is concerned. However, the construction of such units involves the problem that the blade protruding to a negligible extent only is easily damaged, for example, when putting down the same. In addition, there is danger for the user to hurt himself, by way of inadvertence, by the protruding blade.

It is, therefore, the object of the invention to improve a horny skin remover of the type referred to hereinbefore in that, on the one hand, the blade itself be protected, when the skin remover is not used and, on the other hand, cutting injuries due to careless handling be reliably prevented from occurring.

This problem, in the practice of the invention, is solved by a horny skin remover of the afore-mentioned type in that the clamp adjustable in relation to the blade is associated to the header and has at least two adjustable positions, namely the "RELEASE" and the "COVER" positions of the at least one cutting edge.

Accordingly, the conception underlying the invention substantially resides in the double function of the clamp, using it both for attaching and for covering the blade in times of non-use, thereby eliminating a separate blade protection otherwise required, and at the same time insuring that protection of the blade be not forgotten, by inadvertence, as the clamp is required for mounting the blade.

Advantageous embodiments of the horny skin remover are set forth in the dependent claims.

BRIEF DESCRIPTION OF THE DRAWINGS

The above and other features, objects and advantages of this invention will become apparent from the following detailed description of preferred embodiments, taking in conjunction with the accompanying drawings, wherein

FIG. 4 is a front view of the clamp;

FIG. 5 is a side view of the clamp;

FIG. 6 is a rear view of the clamp;

FIG. 7 is a front view of the clamp including a finger-abutment;

DETAILED DESCRIPTION OF PREFERRED EMBODIMENTS

Figure 1:
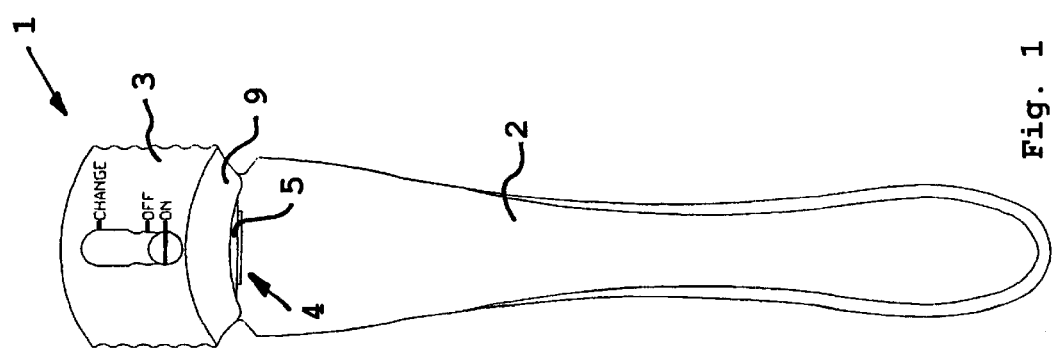
FIG. 1 is a front view of the horny skin remover in the "RELEASE" position of the cutting edge.
Figure 2:
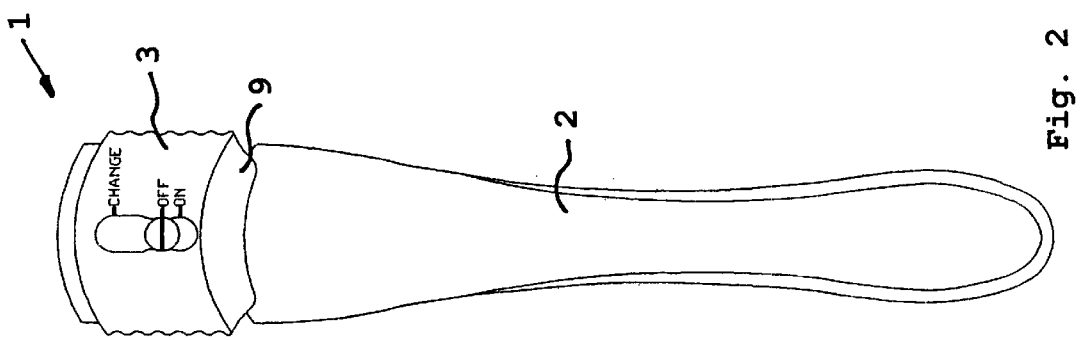
FIG. 2 is a front view of the horny skin remover in the "COVER" position of the cutting edge.

Referring to the drawings, FIGS. 1 and 2 show a horny skin remover comprising a handle 2 and a header 1 mounted thereon, attached to which by means of a clamp 3 is a blade 4 having at least one cutting edge 5. Significantly, the clamp 3 is associated to the header 1 in a manner adjustable relative to the blade 4 and has at least two adjustable positions, namely the "RELEASE" position (FIG. 1) and the "COVER" position (FIG. 2) of the at least one cutting edge 5. In the drawings, the "RELEASE" position is marked by "ON" and the "COVER" position by "OFF".

The phrase "adjustable relative to the blade 4" refers to the fact that the structural association of the clamp 3 to the header 1 is less important to the solution of the problem encountered than the way the clamp 3 is attached to the header enabling it to take at least two adjustable positions. Accordingly, also a clamp 3 can be used that is attached to the header, for example, by a hinged joint (not shown).

Preferably, the clamp 3 is displaceably disposed on the header 1. To that extent, it is designed in the form of a slide as shown, in particular, in FIG. 5. For adjusting the respective position, the clamp 3 is displaced in the axial direction of the horny skin remover. With the position opened as shown in FIG. 1, the cutting edge of the blade 4 is usable for access.

Figure 3:
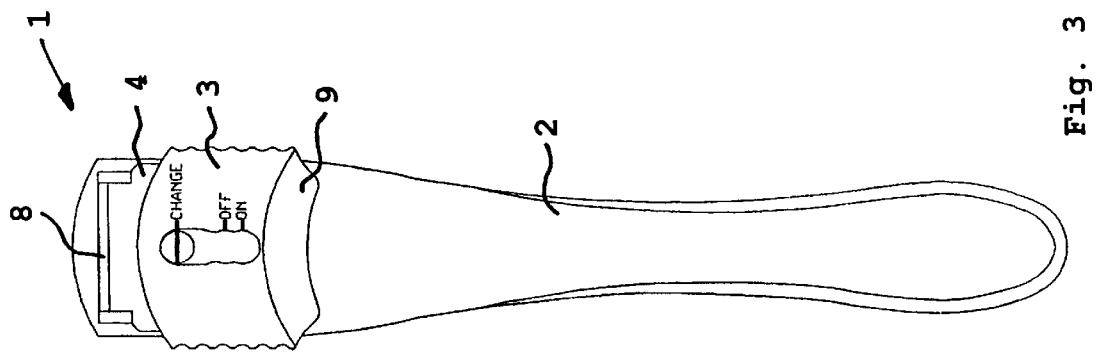
FIG. 3 is a front view of the horny skin remover in the "CHANGE" position of the cutting edge.
Figure 11:
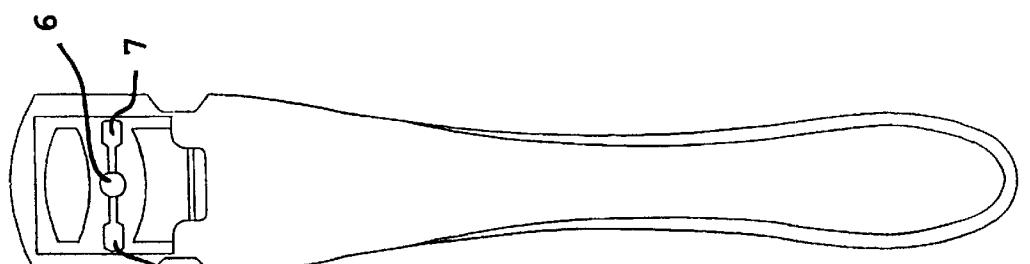
FIG. 11 is a front view of the horny skin remover, with clamp and blade omitted.
Figure 10:
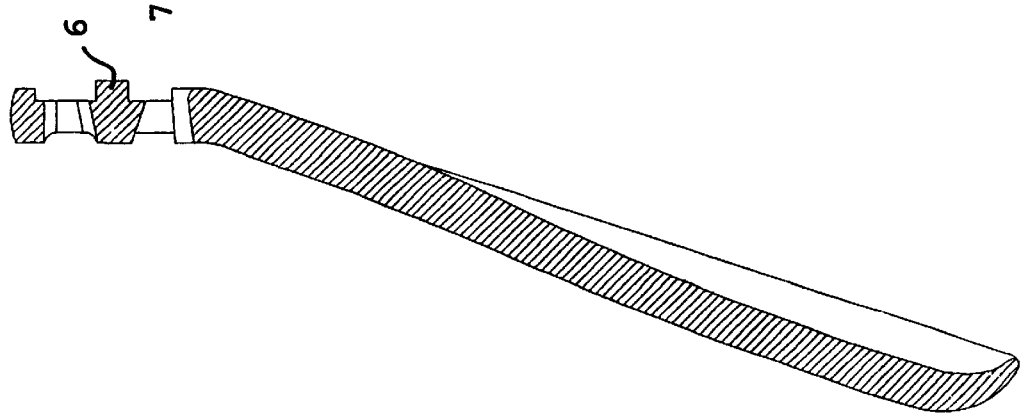
FIG. 10 is a sectional view of the horny skin remover, with clamp and blade omitted.

FIGS. 1, 2 and 3 show another advantageous embodiment according to which the clamp 3 contains a third position of adjustment, namely the "CHANGE" position, wherein the clamp 3 is separable from header 1 and blade 4 is exchangeable.

The phrase "at least partly separable" as used in the dependent claim 3 is in reference to that the clamp 3 is not required to be completely separated from header 1 to fulfill the Change function; to that extent, for example, also an embodiment is permitted wherein the clamp 3 can be laterally folded off, as mentioned hereinbefore.

The clamp 3 separately shown in FIGS. 4 to 6 preferably is in the form of a slightly curved surface 11 having short lateral legs 12 straddling the header 1 at least in part, with the legs 12 on the seizing side being provided with shaped profiles 13 to avoid slipping.

Figure 9:
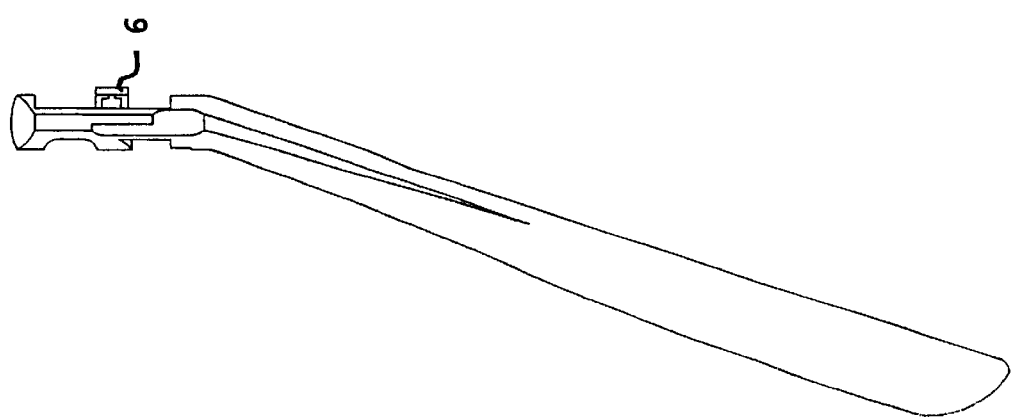
FIG. 9 is a sectional view of the horny skin remover, with clamp and blade omitted.
Figure 8:
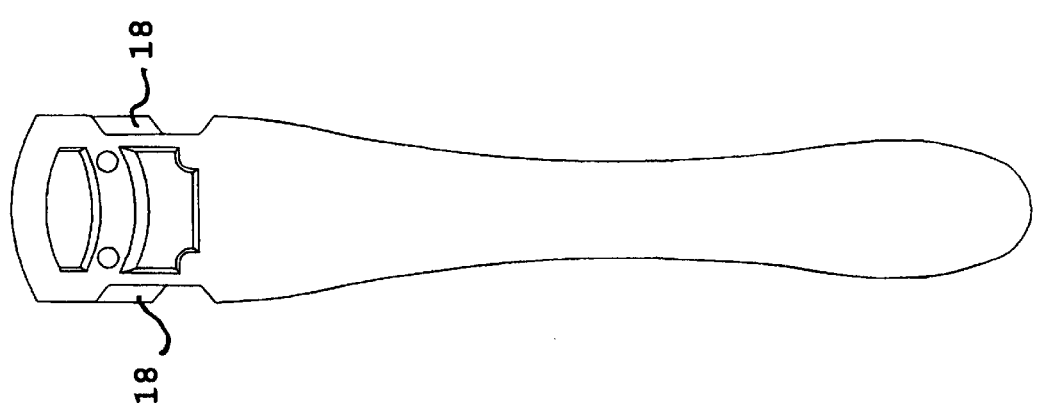
FIG. 8 is a rear view of the horny skin remover, with clamp and blade omitted.

FIGS. 6, 8 and 9 show the way the slide-type clamp 3 is held on the header 1: The lug-shaped projections 17 on the legs 12 of the clamp 3 (see FIG. 6) undercut the webs 18 arranged on both sides longitudinally of the header 1 (see FIG. 8).

To safely displace the clamp 3 without danger of injury it is, moreover, advantageous, as shown in FIG. 7, to provide a finger abutment 10, preferably a thumb abutment.

In the event that the blade 4 has two cutting edges 5 and 8, the second cutting edge 8 of blade 4 is covered by the clamp 3 in the "RELEASE" and "COVER" positions, as shown in FIGS. 1 through 3.

In terms of manufacture, the horny skin remover, except for the blade 4, is completely manufactured by injection molding.

Moreover, provided on header 1 is a pin 6 extending through an aperture within the blade 4, and forming together with a sectional groove 15 a locking element on clamp 5 for fixing the adjustable positions. An additional web 7 arranged on both sides of the pin 6, moreover, prevents the blade 4 from twisting.

Finally, clamp 3, on the side of the cutting edge, is provided with a concave marginal area 9 which, in the release position, releases the center area of the blade 5 but not the marginal areas thereof (see FIG. 1).

What is claimed is:

1. A horny skin remover, comprising a handle with a header mounted thereon attached to which, by means of a clamp, is a blade including at least one cutting edge, wherein the clamp is associated to the header in a manner adjustable relative to the blade, and has at least two adjustable positions, firstly a "RELEASE" and secondly a "COVER" position of the at least one cutting edge.

2. The horny skin remover according to claim 1, wherein the clamp is displaceably arranged on the header.

3. The horny skin remover according to claim 1, wherein the clamp has a third position, namely the "CHANGE" position, wherein the clamp is at least in part separable from the header, and the blade is replaceable.

4. The horny skin remover according to claim 1, wherein the clamp is in the form of a slightly curved surface including short lateral legs at least in part straddling the header.

5. The horny skin remover according to claim 4, wherein the legs, on the seizing side are provided with shaped profiles.

6. The horny skin remover according to claim 1, wherein a finger abutment, preferably a thumb abutment, is provided on the clamp.

7. The horny skin remover according to claim 1, wherein a second cutting edge of the blade is covered by the clamp in both adjustable positions.

8. The horny skin remover according to claim 1, wherein the horny skin remover, except for the blade, is completely made of plastic material.

9. The horny skin remover according to claim 1, wherein a pin is provided on the header, passing through an aperture of the blade and, together with a sectional groove, forms a locking element on the clamp to fix the adjustable positions.

10. The horny skin remover according to claim 1, wherein the clamp, on the side of the cutting edge, contains a concave marginal area which, in the "RELEASE" position releases the central area of the cutting edge but not the marginal areas thereof.

* * * * *